US010597602B2

(12) United States Patent
Kavakka

(10) Patent No.: US 10,597,602 B2
(45) Date of Patent: Mar. 24, 2020

(54) EXTRACTION OF PHYTOSTEROLS FROM TALL OIL SOAP USING A SOLVENT SELECTED FROM DIBROMOMETHANE, BROMOFORM, TETRABROMOMETHANE OR A COMBINATION THEREOF

(71) Applicant: Stora Enso OYJ, Helsinki (FI)

(72) Inventor: Jari Kavakka, Stockholm (SE)

(73) Assignee: Stora Enso OYJ, Helsinki (FI)

( * ) Notice: Subject to any disclaimer, the term of this patent is extended or adjusted under 35 U.S.C. 154(b) by 0 days.

(21) Appl. No.: 16/073,437

(22) PCT Filed: Jan. 26, 2017

(86) PCT No.: PCT/IB2017/050408
§ 371 (c)(1),
(2) Date: Jul. 27, 2018

(87) PCT Pub. No.: WO2017/130127
PCT Pub. Date: Aug. 3, 2017

(65) Prior Publication Data
US 2019/0010420 A1 Jan. 10, 2019

(30) Foreign Application Priority Data
Jan. 29, 2016 (SE) ...................... 1650109

(51) Int. Cl.
*C11B 3/00* (2006.01)
*B01D 11/04* (2006.01)
(Continued)

(52) U.S. Cl.
CPC .............. *C11B 3/006* (2013.01); *B01D 3/143* (2013.01); *B01D 11/0492* (2013.01); *C07J 9/00* (2013.01);
(Continued)

(58) Field of Classification Search
CPC .. C07J 75/00; C07J 9/00; C11B 3/006; B01D 11/0492; B01D 2257/2062
See application file for complete search history.

(56) References Cited

U.S. PATENT DOCUMENTS 2,280,815 A * 4/1942 Fernholz ................. C07J 75/00
252/398
2,573,265 A * 10/1951 Lange ..................... C07J 75/00
552/544
(Continued)

FOREIGN PATENT DOCUMENTS

CA          2319230       3/2002
WO        2008099051      8/2008
(Continued)

OTHER PUBLICATIONS

Jones, W. P., Kinghorn, A. D., "Extraction of Plant Secondary Metabolite," Natural Products Isolation, vol. 864, Feb. 8, 2012, Methods in Molecular Biology, 341-366.
(Continued)

*Primary Examiner* — Yate' K Cutliff
(74) *Attorney, Agent, or Firm* — Greer, Burns & Crain Ltd.

(57) ABSTRACT

The present invention relates to extraction of phytosterols from alkaline tall oil soap which is obtained from the Kraft process black liquor by skimming. In the method according to the present invention, phytosterols are extracted using dibromomethane, bromoform, tetrabromomethane or a combination thereof.

11 Claims, 1 Drawing Sheet

(51) Int. Cl.
    *C11B 3/12*     (2006.01)
    *D21C 11/00*    (2006.01)
    *C07J 9/00*     (2006.01)
    *B01D 3/14*     (2006.01)
    *C07J 75/00*    (2006.01)

(52) U.S. Cl.
    CPC .............. *C07J 75/00* (2013.01); *C11B 3/12* (2013.01); *D21C 11/00* (2013.01); *B01D 2257/2062* (2013.01)

(56) References Cited

U.S. PATENT DOCUMENTS

| | | |
|---|---|---|
| 2,839,544 A | 6/1958 | Greiner et al. |
| 2,963,494 A | 12/1960 | Cunningham et al. |
| 3,840,570 A | 10/1974 | Julian |
| 3,965,085 A | 6/1976 | Holmbom et al. |
| 4,044,031 A | 8/1977 | Johansson et al. |
| 4,265,824 A | 5/1981 | Koskenniska et al. |
| 5,770,749 A | 6/1998 | Kutney et al. |
| 6,770,767 B1 * | 8/2004 | Hamunen ............... C07J 9/00 552/545 |
| 2005/0107582 A1 | 5/2005 | Wong et al. |
| 2006/0166951 A1 | 7/2006 | Sanbom |

FOREIGN PATENT DOCUMENTS

| | | | |
|---|---|---|---|
| WO | WO-2008099051 A2 * | 8/2008 | ........... C11B 13/005 |
| WO | 2009106696 | 9/2009 | |
| WO | WO-2009113935 A1 * | 9/2009 | ............... C07J 9/00 |

OTHER PUBLICATIONS

International Searching Authority, International Search Report, PCT/IB2017/050408, dated Mar. 21, 2017.
International Searching Authority, Written Opinion of the International Searching Authority, PCT/IB2017/050408, dated Mar. 21, 2017.

* cited by examiner

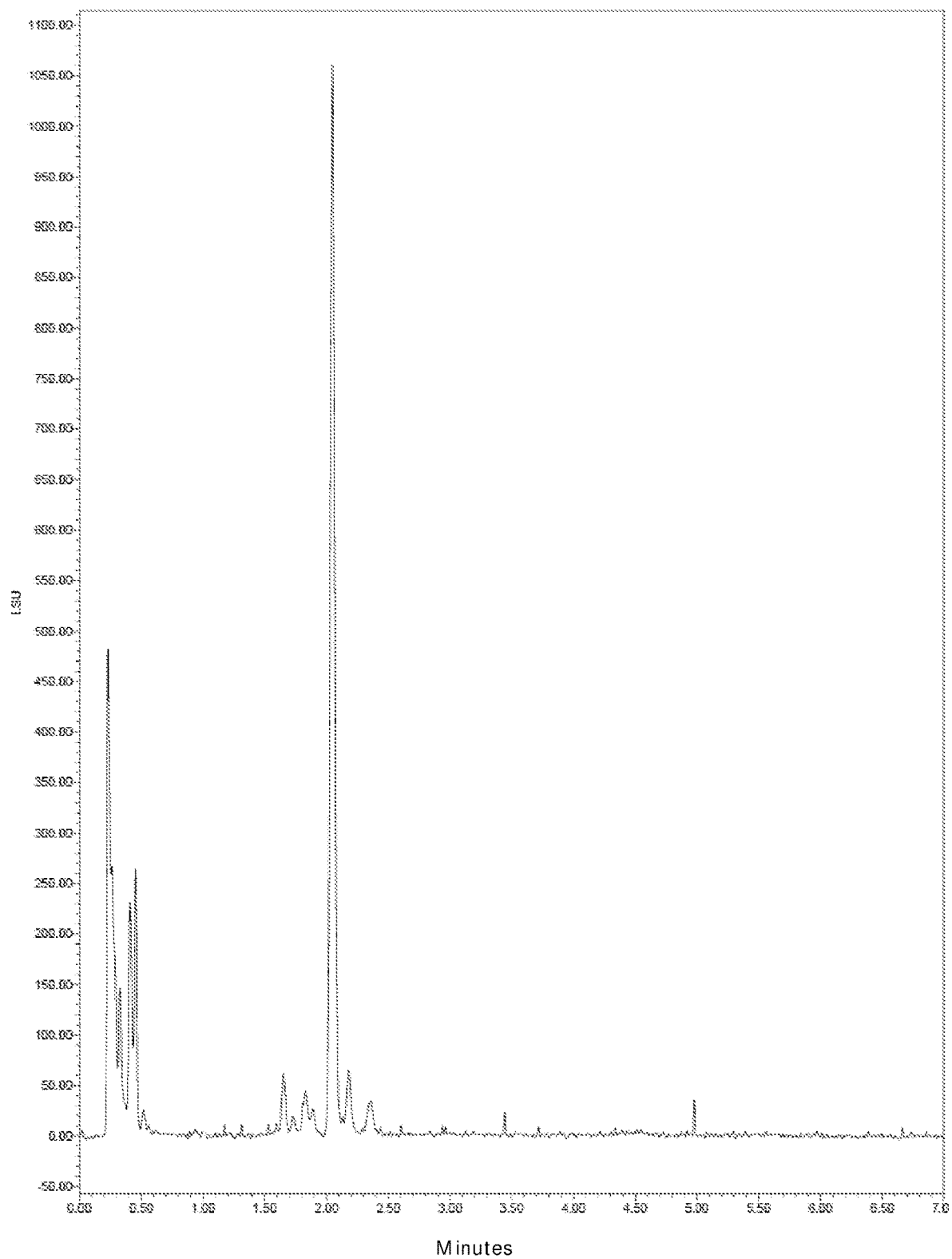

ated January 26, 2017, which claims priority under 35 U.S.C. §§ 119 and 365 to Swedish Application No. 1650109-0, filed Jan. 29, 2016.

EXTRACTION OF PHYTOSTEROLS FROM TALL OIL SOAP USING A SOLVENT SELECTED FROM DIBROMOMETHANE, BROMOFORM, TETRABROMOMETHANE OR A COMBINATION THEREOF

This application is a U.S. National Phase under 35 U.S.C. § 371 of International Application No. PCT/IB2017/050408, filed Jan. 26, 2017, which claims priority under 35 U.S.C. §§ 119 and 365 to Swedish Application No. 1650109-0, filed Jan. 29, 2016.

FIELD OF THE INVENTION

The present invention relates to extraction of phytosterols from alkaline tall oil soap which is obtained from the Kraft process black liquor by skimming. In the method according to the present invention, phytosterols are extracted using dibromomethane, bromoform, tetrabromomethane or a combination thereof.

BACKGROUND

Tall oil soap (TOS) is a by-product of the Kraft process. The soap consists mainly of sodium salts of fatty acids, sodium salts of diterpenic (rosin) acids, free fatty acids, free rosin acids and unsaponifiable neutral compounds such as fatty alcohols, sterols, steryl esters and waxes. The water content of neat soap is typically 25 to 45%, such as 30 to 35%. The pH of the soap is typically in the range of 12 to 13, arising from the presence of entrained black liquor. In industrial practice, soap is routinely acidulated with sulphuric acid to produce crude tall oil (CTO), an article of commerce. Sterols, in particular phytosterols, have several uses, including the use as food additives and as precursors for steroids. Several methods have been reported for the isolation of sterols from tall oil soap. The general method involves the extraction of neat soap with a variety of organic solvents. The presence of entrained black liquor promotes and stabilizes the unwanted water-oil emulsion, which is known to be extremely difficult to break. Consequently, the efficiency of solvent extraction of neat soap for the isolation of sterols is greatly reduced. Holmbom et al. teach in U.S. Pat. No. 3,965,085 the extraction of a mixture of acetone-water soap slurry, with a water-immiscible solvent such as hexane. The aqueous phase contains mainly sodium salts of fatty and resin acids. The organic phase contains mostly unsaponifiables including sterols. In U.S. Pat. No. 4,044,031, Johansson et al. teach the dissolution of soap in a water-immiscible mixture comprising hexane and acetone, extraction of the water-immiscible phase with another solvent mixture comprising methanol or acetone and hexane and water, and isolation of sterols from the methanolic phase by evaporative crystallization. In U.S. Pat. No. 5,770,749, Kutney et al. teach the use of a mixture of ketones, hydrocarbons and water to extract sterols from soap. The hydrocarbon extract is further processed with methanol. However, the complexity of recovering the multi- component spent solvent is very problematic in these processes. Also, recycling highly water soluble solvents such as acetone and methanol from water mixtures is very complicated.

Further examples of methods of obtaining phytosterols are described in US2005/0107582, WO2009/106696 and CA2319230.

There is thus a need for a more efficient method of obtaining phytosterols from tall oil soap.

SUMMARY OF THE INVENTION

It has been found that any of the solvents dibromomethane, tetrabromomethane and bromoform can selectively extract phytosterols from tall oil soap without a need for any emulsion breaking polar organic solvent such as methanol or acetone or similar.

Thus, the present invention is directed to a method for extracting phytosterols from tall oil soap comprising the steps of a) obtaining tall oil soap,
b) mixing the tall oil soap with a solvent selected from dibromomethane, tetrabromomethane, bromoform or a combination thereof, and
c) recovering phytosterols from the solvent extract.

In one embodiment of the present invention, step c) involves separation of phases followed by distillation of the selected solvent with elevated temperature at normal or reduced pressure.

In one embodiment of the present invention, step c) involves precipitation of the phytosterols. The precipitation can be achieved through reducing the temperature or concentrating the sample or by addition of an anti-solvent or any combination thereof.

In one embodiment of the present invention, the phytosterols recovered in step c) are purified by cooling or evaporative crystallization.

In one embodiment of the present invention, dibromomethane is used as extraction solvent.

In one embodiment of the present invention, bromoform is used as an extraction solvent.

In one embodiment of the present invention, dibromomethane or bromomethane or a combination thereof is used as an extraction solvent.

In one embodiment of the present invention, tetrabromomethane is used as an extraction solvent.

In one embodiment of the present invention, a combination of bromoform and dibromomethane is used as extraction solvent.

In one embodiment of the present invention, a combination of bromoform, tetrabromomethane and dibromomethane is used as extraction solvent.

In one embodiment of the present invention, the solvent is recycled. The extraction solvent in the phytosterol fraction can be recycled after isolation of the phytosterols. The extraction solvent adsorbed in the aqueous phase can be recycled through acidulation, phase separation and subsequent distillation.

BRIEF DESCRIPTION OF THE FIGURES

FIG. 1: UPLC chromatogram obtained as described in Example 1.

DETAILED DESCRIPTION

The term "phytosterol" is intended to mean a sterol derived from plants and encompasses all plant sterols and the saturated forms of phytosterols thereof (i.e., phytostanols). Plant sterols fall into one of three categories: 4-desmethylsterols (lacking methyl groups); 4-monomethylsterols (one methyl group); and 4,4-dimethylsterols (two methyl groups) and include, but are not limited to, sitosterol (e.g., [alpha] and [beta] sitosterol), campesterol, stigmasterol, taraxasterol, and brassicasterol. The term "phytostanol" is intended to mean a saturated phytosterol and encompasses, but is not limited to, sitostanol (e.g., [alpha] and

[beta] sitostanol), campestanol, stigmastanol, clionastanol, and brassicastanol. Phytosterols isolated by the methods of the invention may be quantified by any means known in the art.

In one embodiment of the present invention, the dibromomethane, bromoform or a combination thereof is mixed with tall oil soap and the solvent fraction is removed through phase separation achieved e.g. with mixer settler, centrifugation or with temperature change or any combination thereof and the phytosterols are recovered by removal of the solvent by distillation or by addition of anti-solvent or combination thereof.

It has been observed that regardless of the selected extraction solvent, the volume of aqueous fraction was increased by 20-40% after first extraction due to the adsorption of extraction solvent to the lipophilic carboxylic acid salts in aqueous phase.

As the boiling points of the solvents are low, the adsorbed solvent can be recovered later by acidulation, phase separation and subsequent distillation.

According to UPLC/HPLC-analysis, extraction of phytosterols can be accomplished with any of the solvents listed above or a combination thereof. After the phase separation and evaporation of the brominated solvent the crude phytosterol mixture can be purified by crystallization, using methods known in the art. Finally, the phytosterol depleted tall oil soap can be acidified to produce tall oil with high acid number.

The phytosterol crystallization can be performed using methods known in the art, including cooling, concentration by removing some of the solvent by distillation, evaporation to dryness followed by introduction of a solvent or solvent mixture in which the phytosterols only dissolve at elevated temperature followed by cooling or through seeding with phytosterol crystals or by adding anti-solvent.

The phytosterol depleted tall oil soap can be acidified to produce the tall oil in which there would be residual extraction solvent originating from adsorption to the aqueous phase during the extraction. As there is only trace amount of water left in the tall oil after acidulation of the soap followed by a phase separation, it can be distilled to remove the residual extraction solvent. After this distillation, majority of the unsaponifiables (including phytosterols) as well as the extraction solvent have been removed from the tall oil.

The extraction according to the present invention may be carried out at ambient temperature (room temperature), alternatively under moderate heating to a temperature below about 90° C.

The process according to the present invention may be carried out as a batch process or as a continuous process.

EXAMPLES

Example 1

1 g of tall oil soap was mixed with dibromomethane in 1:2 ratio. The phases were separated by centrifugation and the sample was taken from lower (heavier) phase. The sample was evaporated to dryness and analyzed using UPLC-ELSD system with water, methanol and acetonitrile gradient as solvent, using Acquity BEH C18 2.1×50 mm 1.7 μm as column (FIG. 1). Retention time for beta-sitosterol is 2.05 for sample extracted with dibromomethane.

In view of the above detailed description of the present invention, other modifications and variations will become apparent to those skilled in the art. However, it should be apparent that such other modifications and variations may be effected without departing from the spirit and scope of the invention.

The invention claimed is:

1. A process for extracting phytosterols from tall oil soap comprising the steps of:
   a) obtaining tall oil soap,
   b) extracting phytosterols from the tall oil soap by mixing the tall oil soap with a solvent selected from dibromomethane, bromoform, tetrabromomethane, or a combination thereof to provide a solvent extract comprising a mixture of solvent and the phytosterols, and
   c) recovering the phytosterols from the solvent extract, wherein step b) is conducted at a temperature of below 90° C.

2. A process according to claim 1, wherein the solvent in step b) is selected from dibromomethane, bromoform, or a combination thereof.

3. A process according to claim 1, wherein step c) comprises separation of phases followed by distillation of the selected solvent with elevated temperature at normal or reduced pressure.

4. A process according to claim 3, wherein step c) comprises precipitation of the phytosterols.

5. A process according to claim 1, wherein the phytosterols recovered in step c) are purified by crystallization.

6. A process according to claim 1, wherein dibromomethane is used as solvent.

7. A process according to claim 1, wherein bromoform is used as solvent.

8. A process according to claim 1, wherein tetrabromomethane is used as solvent.

9. A process according to claim 1, wherein a combination of bromoform and dibromomethane is used as solvent.

10. A process according to claim 1, wherein a combination of bromoform, dibromomethane and tetrabromomethane is used as solvent.

11. A process according to claim 1, wherein the solvent is recycled after isolation of the phytosterols and the extraction solvent adsorbed in an aqueous phase is recycled through acidulation, phase separation and subsequent distillation.

* * * * *